United States Patent
Huang et al.

(10) Patent No.: US 10,293,016 B2
(45) Date of Patent: May 21, 2019

(54) USE OF INSTANT ASPARAGUS POWDER IN FOOD, MEDICINE AND HEALTH FOOD

(71) Applicant: QINHUANGDAO CHANGSHENG AGROTECH DEVELOPMENT CO., LTD, Qinhuangdao (CN)

(72) Inventors: Yunxiang Huang, Qinhuangdao (CN); Long Cheng, Qinhuangdao (CN); Qipeng Yuan, Qinhuangdao (CN)

(73) Assignee: QINHUANGDAO CHANGSHENG AGROTECH DEVELOPMENT CO., LTD., Hebei (CN)

( * ) Notice: Subject to any disclaimer, the term of this patent is extended or adjusted under 35 U.S.C. 154(b) by 759 days.

(21) Appl. No.: 14/787,391

(22) PCT Filed: Jan. 22, 2014

(86) PCT No.: PCT/CN2014/071111
§ 371 (c)(1),
(2) Date: Jan. 26, 2016

(87) PCT Pub. No.: WO2014/176942
PCT Pub. Date: Nov. 6, 2014

(65) Prior Publication Data
US 2016/0129067 A1    May 12, 2016

(30) Foreign Application Priority Data
Apr. 28, 2013 (CN) .......................... 2013 1 0155662

(51) Int. Cl.
| | | |
|---|---|---|
| *A61K 36/8965* | (2006.01) | |
| *A61K 9/00* | (2006.01) | |
| *A61K 9/19* | (2006.01) | |
| *A61K 9/14* | (2006.01) | |
| *A23L 19/00* | (2016.01) | |
| *A23L 33/105* | (2016.01) | |

(52) U.S. Cl.
CPC .......... *A61K 36/8965* (2013.01); *A23L 19/01* (2016.08); *A23L 33/105* (2016.08); *A61K 9/0095* (2013.01); *A61K 9/146* (2013.01); *A61K 9/19* (2013.01); *A23V 2002/00* (2013.01); *A61K 2236/37* (2013.01); *A61K 2236/51* (2013.01)

(58) Field of Classification Search
None
See application file for complete search history.

(56) References Cited

U.S. PATENT DOCUMENTS

| | | | | |
|---|---|---|---|---|
| 6,280,751 B1 * | 8/2001 | Fletcher | ................. | A61K 8/922 |
| | | | | 424/195.18 |
| 2014/0294998 A1 * | 10/2014 | Chaudhary | .......... | A61K 36/185 |
| | | | | 424/734 |

FOREIGN PATENT DOCUMENTS

| | | | |
|---|---|---|---|
| CN | 101791371 | * | 8/2010 |
| CN | 102293381 | * | 12/2011 |
| CN | 102429184 A1 | | 5/2012 |
| CN | 102511802 A1 | | 6/2012 |
| IN | 2012 MU01513 | * | 5/2014 |
| JP | 2007230870 A1 | | 9/2007 |

OTHER PUBLICATIONS

Vina, D. et al. Herbal Natural Products as a Source of Monoamine Oxidase Inhibitors. Current Topics in Medicinal Chemistry 12: 2131-2144, 2012. (Year: 2012).*
Meena J. et al. Asparagus recemosus Competitively Inhibits in vitro the Acetylcholine and Monoamine Metabolizing Enzymes. Neuroscience Letters 503(1)6-9, 2011. (Year: 2011).*
Zhao Q. et al. Optimization of Ultrasonic Circulating Extraction of Polysaccharides from Asparagus officinalis Using Response Surface Methodology. Int J of Biological Macromolecules 49(2)181-187, Aug. 1, 2011. (Year: 2011).*
Sharma, A. et al. Vital Medicine Asparagus racemosus willd. Current Trends in Biotechnology and Pharmacy 6(2)210-221, Apr. 2012. (Year: 2012).*
Singh, G. et al. Antidepressant Activity of Asparagus racemosus in Rodent Models. Pharmacology, Biochemistry and Behavior 91(3)283-290, 2009. (Year: 2009).*
Luo, G. Nutitional Components of Asparagus and Their Physiological Effects in the Human Body. Sichuan Food and Fermentation 3:47-50, Mar. 1994. (Year: 1994) English translation.*
International Search Report for PCT/CN2014/071111, dated May 14, 2014, 3 pages.
Luo, Guilun, "Nutritional components of asparagus and effect on human physiology," Sichuan Food and Fermentation, (3): 49, 1994.
Zhong, Y. and Liu, X., "Health Function and Utilization of Asparagus," Shangqiu Vicational and Technical College, Sangqiu 476000, Henan, China, Food Research Associate, 2008, 3 pages.

* cited by examiner

*Primary Examiner* — Ralph J Gitomer
(74) *Attorney, Agent, or Firm* — Kilpatrick Townsend & Stockton LLP

(57) ABSTRACT

The present disclosure provides a method for treating or relieving anxiety disorder by administering an effective amount of an asparagus powder, with active ingredients in the asparagus powder including: 15.0% or more of an asparagus saponin, 8% or more of a polysaccharide, 3.0% or more of a polyphenol, and 2.0% or more of a flavone.

4 Claims, No Drawings

USE OF INSTANT ASPARAGUS POWDER IN FOOD, MEDICINE AND HEALTH FOOD

TECHNICAL FIELD

The present invention relates to the field of medicine and health foods, and particularly to use for regulating the nervous system and relieving the mental stresses (relaxing the body and mind) in the field of food, medicines, and health foods.

CROSS-REFERENCE TO RELATED APPLICATIONS

This application is a national phase application under 35 U.S.C. 371 claiming priority to PCT/CN2014/071111, filed Jan. 22, 2014, which application claims priority to CN 201310155662.1, filed Apr. 28, 2013, the teachings of which are hereby incorporated by reference in their entireties for all purposes.

BACKGROUND ART

At present, the nervous and psychological stresses have become one of the most serious health problems in the 21th century. The psychological stress refers to a response which an individual generates to the body, psychology, emotion, and action to seek for recovering the balance when the individual suffers a threatening stimulation from the outside which destroys the balance of the individual and cannot be overcome by the individual himself. The response of a person to stress has three stages: shock, resistance, and exhaustion according to Doctor HANS SELYE who studied the psychological and physiological response to stress. Heart failure is one of the most serious consequences of the work stress, as one typical problem of occupational psychological health. This is a state in which the body, emotion, and psychology are exhausted.

Generalized anxiety includes a group of psychological disorders common in clinic, with which a patient would feel damage to his neurocognitive functions such as attention, memory, and reagency, and present the symptoms such as anxiety, depression, nervousness, and obsessive-compulsion. Such lasting psychological conflict hinders the psychological function or social function of the patient, but does not have any confirmable organic pathological basis. Anxiety and depressive disorder are mental diseases which severely threaten people's health. The latest research data shows that the morbidity of anxiety disorder reaches up to 10% in the aged and 2%-5% in the general population; and the morbidity of depression in the adolescent is about 2%, moreover, the morbidity gradually increases with age. The economic loss caused by these emotional disorders is quite heavy each year, and the severe social issues such as suicide will be caused.

As the modern people suffer from great stresses (work stress, interpersonal stress, emotional stress, etc.), and are busy and lack of sleep, the long-term stresses will deteriorate the immunity of the organism. At present, these mental disorders are handled with a plurality of measures: self-regulation and distraction, psychological consultation and counseling, non-drug intervention, and drug therapy. Therefore, there is still a need in the art to develop medicines or health foods which can regulate the nervous system and relieve the mental stresses (relaxing the body and mind).

An asparagus powder is disclosed in the Chinese patent No. 201110278589.8, entitled "An Instant Asparagus Powder" filed by the applicant Qinhuangdao Changsheng Agrotech Development Co., Ltd on Sep. 20, 2011, and this patent document is incorporated herein by reference in its entity. In this document, the asparagus powder is prepared through the method including following steps:

crushing a fresh asparagus (dried asparagus or old asparagus stems and asparagus straws) as raw material; placing the crushed material into an ultrasonic extraction tank; adding water, which is 0.5-20 times of the crushed material in volume for soaking for 10-60 minutes, boiling for 15-120 minutes by a conventional or high-pressure or ultrasonic method to obtain an extracting solution; placing the extracting solution in a vacuum concentration tank for undergoing the vacuum concentration until the content of solid materials reaches 10-50%; cooling for 10-200 minutes at a temperature below 15° C.; centrifugally filtrating to obtain a concentrated extracting solution; adding malto dextrin into the concentrated extracting solution with the content of the malto dextrin as 0-200% of the content of dry substances; and spray-drying at a temperature of 140-190° C. in a spray-drying tower or freeze-drying until the water content is less than or equal to 5% so as to obtain the asparagus powder.

In the above, both the ratio of the malto dextrin added and the water content after drying are calculated in weight percentage. The contents of asparagus saponin, polysaccharide, polyphenol, and flavone, which are the ingredients in the asparagus powder, reach 15.0% or more, 8% or more, 3.0% or more, and 2.0% or more, respectively.

DISCLOSURE OF THE INVENTION

Inventors of the present invention found that the asparagus powder of the present invention has the functions of regulating the nervous system, relieving the mental stresses, and relaxing the body and mind, and has a broad application prospect in the aspects of treating anxiety and depressive mental disorders.

Therefore, in the first aspect, the present invention provides use of an asparagus powder in preparing medicines for the treatment of anxiety and depressive mental disorders, with active ingredients contained in the asparagus powder including: 15.0% or more of an asparagus saponin, 8% or more of a polysaccharide, 3.0% or more of a polyphenol, and 2.0% or more of a flavone.

In one embodiment, the asparagus powder is prepared through the following process:

crushing a fresh asparagus or a dried asparagus or old asparagus stems or asparagus straws, as raw material; placing the crushed material into an ultrasonic extraction tank, adding water which is 0.5-20 times of the crushed material in volume for soaking for 10-60 minutes, boiling for 15-120 minutes by a conventional or high-pressure or ultrasonic method to obtain an extracting solution;

placing the extracting solution in a vacuum concentration tank for undergoing vacuum concentration until content of solid materials reaches 10-50%, cooling for 10-200 minutes at a temperature below 15° C.; centrifugally filtrating to obtain a concentrated extracting solution; adding malto dextrin into the concentrated extracting solution, with the content of the malto dextrin as 0-200% of the content of dry substances; and spray-drying at a temperature of 140-190° C. in a spray-drying tower or freeze-drying until water content is less than or equal to 5% so as to obtain a finished product.

In another aspect, the present invention provides use of an asparagus powder in preparing health foods for relieving anxiety and depressive mental disorders, with active ingredients in the asparagus powder including: 15.0% or more of an asparagus saponin, 8% or more of a polysaccharide, 3.0% or more of a polyphenol, and 2.0% or more of a flavone.

In one embodiment, the asparagus powder is prepared through the following process:

crushing a fresh asparagus or a dried asparagus or old asparagus stems or asparagus straws, as raw material; placing the crushed material into an ultrasonic extraction tank; adding water which is 0.5-20 times of the crushed material in volume for soaking for 10-60 minutes, boiling for 15-120 minutes by a conventional or high-pressure or ultrasonic method to obtain an extracting solution;

placing the extracting solution in a vacuum concentration tank for undergoing vacuum concentration until content of solid materials reaches 10-50%; cooling for 10-200 minutes at a temperature below 15° C.; centrifugally filtrating to obtain a concentrated extracting solution; adding malto dextrin into the concentrated extracting solution with the content of malto dextrin as 0-200% of the content of dry substances; and spray-drying at a temperature of 140-190° C. in a spray-drying tower or freeze-drying until water content is less than or equal to 5% so as to obtain a finished product.

In another aspect, the present invention provides a method for treating or relieving anxiety and depressive mental disorders, the method including: administering asparagus powders to a subject in need, having active ingredients including: 15.0% or more of an asparagus saponin, 8% or more of a polysaccharide, 3.0% or more of a polyphenol, and 2.0% or more of a flavone.

In one embodiment, the asparagus powder is prepared through the following process:

crushing a fresh asparagus or a dried asparagus or old asparagus stems or asparagus straws, as raw material; placing the crushed material into an ultrasonic extraction tank; adding water which is 0.5-20 times of the crushed material in volume for soaking for 10-60 minutes, boiling for 15-120 minutes by a conventional or high-pressure or ultrasonic method to obtain an extracting solution;

placing the extracting solution in a vacuum concentration tank for undergoing vacuum concentration until content of solid materials reaches 10-50%; cooling for 10-200 minutes at a temperature below 15° C.; centrifugally filtrating to obtain a concentrated extracting solution; adding malto dextrin into the concentrated extracting solution, with the content of the malto dextrin as 0-200% of the content of dry substances; and spray-drying at a temperature of 140-190° C. in a spray-drying tower or freeze-drying until water content is less than or equal to 5% so as to obtain a finished product.

In another aspect, the present invention provides an asparagus powder for treating or relieving anxiety and depressive mental disorders, with active ingredients including: 15.0% or more of an asparagus saponin, 8% or more of a polysaccharide, 3.0% or more of a polyphenol, and 2.0% or more of a flavone.

In one embodiment, the asparagus powder is prepared through the following process:

crushing a fresh asparagus or a dried asparagus or old asparagus stems or asparagus straws, as raw material; placing the crushed material into an ultrasonic extraction tank, adding water which is 0.5-20 times of the crushed material in volume for soaking for 10-60 minutes, boiling for 15-120 minutes by a conventional or high-pressure or ultrasonic method to obtain an extracting solution;

placing the extracting solution in a vacuum concentration tank for undergoing vacuum concentration until content of solid materials reaches 10-50%; cooling for 10-200 minutes at a temperature below 15° C.; centrifugally filtrating to obtain a concentrated extracting solution; adding malto dextrin into the concentrated extracting solution, with the content of the malto dextrin as 0-200% of the content of dry substances, and spray-drying or freeze-drying at a temperature of 140-190° C. in a spray-drying tower until a water content is less than or equal to 5% so as to obtain a finished product.

The tests proved that the asparagus powder of the present invention can effectively relieve the nervous state, and achieve the function to notably regulate the nervous system, and a wide application prospect in the aspects of treating anxiety and depressive mental disorders.

DETAILED DESCRIPTION OF EMBODIMENTS

Below, the present invention is further described with reference to the examples. It should be understood that the following examples are intended for better understanding and implementation of the present invention by a person skilled in the art, rather than limiting the scope of the present invention. In the following respective examples, unless indicated otherwise, the temperatures used are the room temperature, the pressures used are the atmospheric pressure, all the percentages or fractions used are weight percentages or fractions, and all the reagents used are commercially available products.

EXAMPLES

Preparation Examples

Preparation Example 1

Asparagus Powder Medicine

The (dry or fresh) asparagus, as raw material, was subjected to rinsing, crushing, boiling in water, filtration to remove slag, concentration, centrifuging, membrane filtration, and spray-drying, to prepare asparagus powders enriched in an asparagus saponin, and the asparagus powders were combined with other raw materials to prepare a medicine relieving mental stresses, wherein the amount of the asparagus saponin contained reaches 0.75-1.25 g.

Preparation Example 2

Asparagus Powder Solid Beverage

The (dry or fresh) asparagus, as raw material, was subjected to rinsing, crushing, boiling in water, filtration to remove slag, concentration, centrifuging, membrane filtration, and spray-drying to prepare asparagus powders enriched in an asparagus saponin, i.e. a solid beverage, wherein the content of the effective ingredient, the asparagus saponin, reaches 12.5%. The drinking dosage per day is 6-10 g.

Preparation Example 3

Asparagus Powder Dairy Product

The (dry or fresh) asparagus, as raw material, was subjected to rinsing, crushing, boiling in water, filtration to remove slag, concentration, centrifuging, membrane filtration, and spray-drying to prepare asparagus powders enriched in an asparagus saponin, and asparagus powders were added to milk or yoghourt to directly dissolve, to prepare a dairy product relieving the mental stresses, wherein the amount of the asparagus saponin contained reaches 0.5-1.25 g.

Preparation Example 4

Asparagus Powder Cosmetic Product

The (dry or fresh) asparagus, as raw material, was subjected to rinsing, crushing, boiling in water, filtration to remove slag, concentration, centrifuging, membrane filtration, and spray-drying to prepare asparagus powders enriched in an asparagus saponin, and asparagus powders were mixed with collagen powders to obtain a cosmetic product relieving the mental stresses, wherein the amount of the asparagus saponin contained reaches 0.5-1.25 g.

Preparation Example 5

Asparagus Powder Liquid Beverage

The (dry or fresh) asparagus, raw material, was subjected to rinsing, crushing, boiling in water, filtration to remove slag, concentration, centrifuging, membrane filtration, and spray-drying to prepare asparagus powders enriched in an asparagus saponin, and the asparagus powders were added to a beverage to directly dissolve, to obtain a liquid beverage relieving the mental stresses, wherein the amount of the asparagus saponin contained reaches 0.5-1.25 g.

Preparation Example 6

Asparagus Powder Health Foods

The (dry or fresh) asparagus, as raw material, was subjected to rinsing, crushing, boiling in water, filtration to remove slag, concentration, centrifuging, membrane filtration, spray-drying, and packaging, to prepare asparagus powders enriched in an asparagus saponin, and the asparagus powders were combined with other raw materials to prepare health foods relieving the mental stresses, wherein the amount of the asparagus saponin contained reaches 0.75-1.25 g.

Test Examples

A plurality of animal models were used in animal experiments to study its function of regulating the mental system. The asparagus powder has certain function of relieving the animal anxiety (model) caused by the acute and chronic stress models, can prominently decrease the serum cortisol concentration (an important biochemical index in the stress state) in the stress-response state, reduces the locomotor activity of the mouse, and has certain function of inhibiting the hyperactivity of the central nervous system in the unfamiliar environment. The antianxiety function may be associated with its rising of the level of 5-HT (5-hydroxytryptamine) in vivo.

Test Example 1

Elevated Plus Maze Model (Elevated Plus Maze, "EPM" for Short) Test

The elevated plus maze has been widely used in anxiety experiments of the small rodent. This system is used to detect the situation of decreasing animals' inherent aversion to a high position and a open field, after using the anxiety drug. The rodent (e.g. rat, mouse), which have the exploratory behavior, will actively explore the open arms after placed in the elevated plus maze, but fear the high and open environment in the open arms. The antianxiety drug increases the open-arm exploratory activities, while the anxiety drug has the opposite effect.

The elevated plus maze has a pair of open arms and a pair of closed arms. The animal, after a period of time of adaptation, is rapidly placed in the central platform of the EPM in such a way that its head directly faces one of the open arms. A tracking camera is used to record following: (1) times of entering the open arm (open arm entry, OE) within 5 minutes, wherein it is considered as one time of entering an open arm when all the four paws of the rat have entered any open arm, and meanwhile this entry activity is finished when one paw completely withdraws from this arm; (2) duration of staying in an open arm (open arm time, OT) within 5 minutes, wherein the unit of the duration of staying in an open arm is "second"; (3) times of entering a closed arm (close arm entry, CE) within 5 minutes, wherein it is considered as one time of entering a closed arm when all the four paws of the rat have entered any closed arm; (4) duration of staying in a closed arm (close arm entry, CT) within 5 minutes, wherein the unit of duration of staying in a closed arm is "second". The following is calculated from (1)-(4), respectively:

(1) the total number of the times of the open arm entry and the closed arm entry (OE+CE): representing the motion vitality of the rat;

(2) the ratio of the times of the open arm entry (OE %); the times of the open arm entry/(OE+CE)×100%;

(3) the ratio of the duration of staying in the open arms (OT %), i.e. the duration of staying in the open arms/(OT+CT)×100%. Each rat is tested for 5 minutes. OE % and OT % represent the indices of the antianxiety effect.

The test results indicate: the asparagus powder and diazepam (DZP) and casein peptide (CTH) with the dosage of administration can increase the values of OT % and OE % without increasing the total number of the times of entering arms (the total number of the times of entering arms represents the motion vitality of the animal), indicating that the asparagus powder has a prominent ($P<0.05$) antianxiety function on this anxiety model. See the results in Table-1

TABLE 1

Effect of *Asparagus* Powder in EPM Test of Mouse

| Experimental Group | Dosage | OE + CE (times) | OE (%) | OT (%) |
|---|---|---|---|---|
| Negative Control | — | 10.8 ± 3.9 | 22.8 ± 5.9 | 20.1 ± 4.5 |
| DZP (diazepam) | 3 mg/Kg | 12.9 ± 5.2 | 40.9 ± 5.2* | 42.3 ± 5.7* |
| CTH (casein peptide) | 30 mg/Kg | 12.2 ± 6.1 | 32.2 ± 6.1 | 33.5 ± 4.6* |
| IAP-l (*asparagus* powder of low dosage) | 0.6 g/Kg | 11.6 ± 4.8 | 26.6 ± 10.8 | 28.6 ± 5.4 |
| IAP-m (*asparagus* powder of medium dosage) | 1.5 g/Kg | 10.3 ± 4.3 | 30.3 ± 8.3 | 34.3 ± 6.3* |
| IAP-h (*asparagus* powder of high dosage) | 3.0 g/Kg | 13.5 ± 5.1 | 35.5 ± 10.1 | 36.5 ± 7.8* |

The data is represented by a mean value±standard deviation (n=10). (*: representing $p<0.05$ compared with the negative control group)

Test Example 2

Chronic Emotional Stress-Response Model (CSM) Test

The chronic emotional stress-response model takes as an emotional stress-response resource an uncertain stimulation of drinking by an empty bottle, so as to investigate the influence which the emotional stress of 14 days exerts on the behaviors, and neuroendocrine and immune functions of the rats. In the present model, the emotions experienced by the animals have a more close relation with anger or anxiety, and all of the behaviors and neuroendocrine and immune responses change notably, which can reflect the emotional responses and the abnormal condition of mood caused by the stress-responses of different degrees and different types, and can be used to simulate the specific stressful moods of human beings, such as anger or anxiety.

After adaptation for one week, the rats were randomly grouped. Except the normal group, the model groups were fed in individual cages and subjected to the uncertain stimulation of drinking by an empty bottle to establish the anxiety stress models. The specific method is as follows: the training of timely feeding water lasts for 7 days, that is, water was being given to the animals for 10 minutes every day at 9:00-9:10 and 17:00-17:10, and at other times, the water bottles were taken away, without water given. After the period of timely feeding water was ended, the stress-response experiment started, wherein the uncertain stimulation of the empty bottle was given once or twice a day in the above two periods of time for two weeks. The normal group was not subjected to any treatment, and was fed with water and food freely. The behaviors observed included attacking (biting or attacking the empty bottle and the cage), exploratory (moving around and visiting the place where the water bottle was located), and grooming behaviors (combing fur and washing face). The specific method was: the 10 minutes of the empty bottle stimulation was equally divided into 10 periods of time, the above-mentioned three types of behaviors of each rat were recorded in each period of time, wherein it was marked as "1" if the behavior appears, otherwise it was marked as "0". The total score obtained in the observation within 10 minutes was between 0 and 10. The score was obtained by averaging the observation results of two observers, with one person under double-blind control. The average score of the first 3 days and the last 3 days of the 14 observation days was used for statistical analysis. The samples were gathered when the experiment was ended to detect the neuroendocrine and immune indices.

The normal control group was not subjected to any treatment; all the other groups were subjected to the stimulation. No medicine was given to the model group; the asparagus powder of 0.6 g/Kg, 1.5 g/Kg, and 3.0 g/Kg was given to the tested group; CTH (LACTIUM™, Ingredia, Arras, France) of 30 mg/Kg and diazepam of 3 mg/Kg were given to the positive control group.

The following behaviors were observed in the test: (1) times of attacking behaviors, (2) times of exploratory behaviors, (3) times of grooming behaviors, and the change of the animal weight.

The following endocrine levels were detected in the test: (1) plasma cortisol concentration, (2) catecholamine level, (3) 5-hydroxytryptamine level.

Analysis of Test Results:

I. Asparagus powders with the dosage of administration can reduce the action times of the attacking, exploratory, and grooming behaviors of the anxious animals, indicating that the asparagus powder tends to have the antianxiety function on this anxiety model, and the statistical results are not varied significantly ($P>0.05$). See the results in Table-2.

TABLE 2

Influence of *Asparagus* Powder on Behavior of Mouse in CSM Test

| Experimental Group | Dosage | Attacking Behavior (%) | Exploratory Behavior (%) | Grooming Behavior (%) |
|---|---|---|---|---|
| Positive Control | — | 0.18 ± 0.49 | 0.70 ± 0.57 | 1.88 ± 0.32 |
| Negative Control | — | 2.56 ± 2.09 | 2.44 ± 0.88 | 2.38 ± 1.16 |
| DZP | 3 mg/Kg | 0.69 ± 0.52 | 1.09 ± 0.52 | 1.78 ± 1.06 |
| CTH | 30 mg/Kg | 1.35 ± 1.12 | 1.56 ± 0.37 | 1.94 ± 0.66 |
| IAP-l | 0.6 g/Kg | 2.06 ± 1.84 | 1.88 ± 0.78 | 2.05 ± 0.46 |
| IAP-m | 1.5 g/Kg | 1.63 ± 1.38 | 1.31 ± 0.82 | 1.75 ± 1.20 |
| IAP-h | 3.0 g/Kg | 1.13 ± 1.11 | 1.56 ± 0.09 | 1.78 ± 1.60 |

The data is represented as a mean value±standard deviation (n=10). (*: representing $p<0.05$ compared with the control groups)

II. Asparagus powders and diazepam with the dosage of administration do not have a notable influence on the change of concentration of the main neurotransmitter in the hippocampus in the brain, while the asparagus powder tends to raise the concentrations of 5-hydroxytryptamine and dopamine (DA) on this anxiety model, and the statistical results are not varied notably ($P>0.05$). See the results in Table-3.

TABLE 3

Level of Neurotransmitter in Hippocampus of Rat in CSM Test

| Experimental Group | Dosage | 5-hydroxytryptamine (ng/mL) | Dopamine (ng/mL) | NE (norepinephrine) (pg/mL) | NA (epinephrine) (pg/mL) |
|---|---|---|---|---|---|
| Positive Control | — | 0.390.20 | 11.44 ± 2.53 | 0.076 ± 0.058 | 27.17 ± 6.80 |
| Negative Control | — | 0.290.10 | 9.542 ± .93 | 0.104 ± 0.048 | 40.97 ± 13.25 |
| DZP | 3 mg/Kg | 0.350.18 | 11.38 ± 4.33 | 0.080 ± 0.053 | 37.22 ± 10.05 |
| IAP | 3.0 g/Kg | 0.450.19 | 9.44 ± 1.16 | 0.155 ± 0.057 | 37.42 ± 9.67 |

The data is represented as a mean value±standard deviation (n=10). (*: representing $p<0.05$ compared with the negative control group)

III. Asparagus powders with the dosage of administration can change the content of the main neurotransmitter in the serum of the anxious animal, and notably decrease the concentration of serum cortisol and raise the concentration of 5-hydroxytryptamine in serum, and the statistical results are varied notably ($P>0.05$). See the results in Table-4.

TABLE 4

Level of Neurotransmitter in Serum of Rat in CSM Test

| Experimental Group | Dosage | COR (cortisol) (ng/mL) | 5-HT (ng/mL) | DA (ng/mL) | NE (pg/mL) | NA (pg/mL) |
|---|---|---|---|---|---|---|
| Positive Control | — | 26.18 ± 3.95* | 1.15 ± 0.16* | 7.10 ± 1.70 | 0.86 ± 0.15 | 15.11 ± 0.72 |
| Negative Control | — | 49.94 ± 7.26 | 0.86 ± 0.15 | 5.45 ± 0.76 | 1.15 ± 0.16 | 15.08 ± 0.71 |
| DZP | 3 mg/Kg | 28.94 ± 6.36* | 1.12 ± 0.13* | 6.00 ± 1.70 | 1.00 ± 0.13 | 14.67 ± 0.36 |
| CTH | 30 mg/Kg | 31.36 ± 8.44 | 1.02 ± 0.14 | 5.38 ± 1.66 | 1.02 ± 0.14 | 14.72 ± 0.56 |
| IAP-l | 0.6 g/Kg | 33.35 ± 6.42* | 1.03 ± 0.12 | 6.05 ± 1.24 | 1.03 ± 0.12 | 14.89 ± 1.28 |
| IAP-m | 1.5 g/Kg | 32.87 ± 4.59* | 0.97 ± 0.19 | 5.87 ± 1.92 | 0.97 ± 0.19 | 14.93 ± 0.42 |
| IAP-h | 3.0 g/Kg | 29.97 ± 2.67* | 1.0 ± 70.16* | 6.25 ± 1.19 | 1.07 ± 0.16 | 15.59 ± 1.81 |

The data is represented as a mean value±standard deviation (n=10). (*: representing p<0.05 compared with the negative control group)

Test Example 3

Analysis of Times of Locomotor activities

The condition of the locomotor activity of an animal reflects the functional status of its central nervous system. The central stimulant drug can prominently increase the locomotor activity but decrease the exploratory behavior, and a certain dosage of antipsychotic drug can decrease the exploratory behavior without influencing the locomotor activity. A YLS-1A multi-functional mouse locomotor activity recorder is used to record the situation of locomotor activity of the mouse at different points of time after drug administration.

The test results indicate: asparagus powders and diazepam with the dosage of administration can decrease the times of locomotor activities of the mouse, prominently reduce the times of locomotor activities of the mouse at the two periods of time, namely, 30 minutes and 60 minutes, and the statistical results are varied notably (P>0.05). See the results in Table-5.

TABLE 5

Influence of IAP on Times of Locomotor Activity among Behaviors of Rat

| Experimental Group | Dosage | 15-20 min (times) | 30-35 min (times) | 60-65 min (times) |
|---|---|---|---|---|
| Negative Control Group | — | 86 ± 35 | 64 ± 15 | 53 ± 9 |
| DZP | 3 mg/Kg | 48 ± 46 | 32 ± 16* | 24 ± 6* |
| IAP-l | 0.6 g/Kg | 65 ± 42 | 55 ± 12 | 40 ± 4* |
| IAP-m | 1.5 g/Kg | 57 ± 35 | 47 ± 15* | 38 ± 5* |
| IAP-h | 3.0 g/Kg | 58 ± 37 | 42 ± 11* | 32 ± 7* |

The data is represented as a mean value±standard deviation (n=10). (*: representing p<0.05 compared with the negative control group).

Foretaste Test of Human Beings.

Test Example 4

Influence of Asparagus Powder on Sleep Quality of Human Beings

How to eat it: once a day before supper for two weeks.

TABLE 6

Influence of *Asparagus* Powder on Sleep Quality of Human Beings

| Dosage (gram per day) | Edible Time | Time Required to Fall Asleep (min) | Sleeping Duration (h) | Sleep Efficiency (%) | Times of Waking-ups During Night (times) |
|---|---|---|---|---|---|
| 1 | Before Eating | 81.0 ± 39.7 | 4.7 ± 0.9 | 63.3 ± 10.8 | 5.6 ± 2.2 |
| | One Week | 64.0 ± 34.8 | 5.3 ± 0.8** | 72.9 ± 9.1** | 4.9 ± 1.8 |
| | Two Weeks | 39.8 ± 14.4** | 6.0 ± 0.5** | 80.8 ± 7.4** | 3.5 ± 1.5** |
| | Three Weeks | 28.8 ± 11.8** | 6.5 ± 0.7** | 87.8 ± 5.7** | 3.1 ± 1.4** |
| 1.5 | Before Eating | 97.0 ± 11.1 | 4.2 ± 0.9 | 57.3 ± 14.5 | 6.3 ± 2.1 |
| | One Week | 54.02 ± 2.2* | 5.5 ± 0.6** | 74.7 ± 9.9* | 4.3 ± 1.6** |
| | Two Weeks | 42.0 ± 10.3** | 5.9 ± 0.4** | 82.2 ± 4.2** | 2.8 ± 0.7** |
| | Three Weeks | 38.0 ± 10.3** | 6.1 ± 0.4** | 83.8 ± 5.9** | 2.6 ± 0.7** |
| 2 | Before Eating | 112.5 ± 39.7 | 3.6 ± 0.8 | 57.7 ± 9.1 | 5.5 ± 2.2 |
| | Three days | 84.5 ± 41.1 | 4.8 ± 0.6 | 68.3 ± 10.0 | 4.7 ± 1.7 |
| | One Week | 62.0 ± 23.1** | 5.6 ± 0.5** | 77.9 ± 9.3** | 3.4 ± 1.5** |
| | Two Weeks | 56.5 ± 19.8** | 5.8 ± 0.7** | 81.3 ± 9.7** | 3.4 ± 1.5** |

(\* representing: having a notable difference compared with the situation before eating (p<0.05); \*\* representing: an extremely notable difference compared with that the situation before eating (p<0.01).

The human foretaste test indicates that the asparagus powder can prominently improve the sleep quality, which is reflected in reducing the time required to fall asleep, increasing the sleeping duration, improving the sleep efficiency, and reducing the times of waking-ups during night.

As seen from the above examples, the asparagus powder of the present invention is safe to eat, has the effect of rapidly regulating the nervous system and easy administration, and has a wide prospect for the treatment of mental disorders such as irritability, inattention, memory deterioration, insomnia, anxiety, and depression caused by endurance of excessive stresses.

INDUSTRIAL APPLICABILITY

The asparagus powder compositions of the present invention can be prepared and applied by industry mean, and can be easily used for preparing drugs or health foods of various administration routes. The asparagus powder of the present invention can efficiently regulate emotions, relieve various stresses so as to improve the sleep quality so that the organism recovers to the normal state, can be used in various aspects such as regulating the nervous system and relieving the mental stresses (relieving the body and mind), and has the industrial applicability.

The invention claimed is:

1. A method for treating anxiety disorder, the method comprising: administering an effective amount of asparagus powder comprising: 15.0% or more of an asparagus saponin, 8% or more of a polysaccharide, 3.0% or more of a polyphenol, and 2.0% or more of a flavone, to thereby treat anxiety disorder.

2. The method according to claim 1, wherein the asparagus powder is prepared through a process including:
crushing a fresh asparagus or a dried asparagus or old asparagus stems or asparagus straws, as raw material, placing the crushed material into an ultrasonic extraction tank, adding water which is 0.5-20 times of the crushed material in volume for soaking for 10-60 minutes, boiling for 15-120 minutes by a conventional or high-pressure or ultrasonic method to obtain an extracting solution; and placing the extracting solution in a vacuum concentration tank for undergoing vacuum concentration until content of solid materials reaches 10-50%, cooling for 10-200 minutes at a temperature below 15° C., centrifugally filtrating to obtain a concentrated extracting solution; adding maltodextrin into the concentrated extracting solution with the content of the maltodextrin as 0-200% of content of dry substances, and spray-drying at a temperature of 140-190° C. in a spray-drying tower or freeze-drying until content of water is less than or equal to 5% so as to obtain a finished product.

3. A method for relieving anxiety disorder, the method comprising: administering an effective amount of health food comprising an asparagus powder, wherein the asparagus powder comprises 15.0% or more of an asparagus saponin, 8% or more of a polysaccharide, 3.0% or more of a polyphenol, and 2.0% or more of a flavone, to relieve anxiety disorder.

4. The method according to claim 3, wherein the asparagus powder is prepared through a process including:
crushing a fresh asparagus or a dried asparagus or old asparagus stems or asparagus straws as raw material, placing the crushed material into an ultrasonic extraction tank, adding water which is 0.5-20 times of the crushed material in volume for soaking for 10-60 minutes, boiling for 15-120 minutes by a conventional or high-pressure or ultrasonic method to obtain an extracting solution; and placing the extracting solution in a vacuum concentration tank for undergoing vacuum concentration until content of solid materials reaches 10-50%, cooling for 10-200 minutes at a temperature below 15° C., centrifugally filtrating to obtain a concentrated extracting solution; adding maltodextrin into the concentrated extracting solution, with content of the concentrated extracting solution as 0-200% of content of dry substances, and spray-drying at a temperature of 140-190° C. in a spray-drying tower or freeze-drying until water content is less than or equal to 5% so as to obtain a finished product.

\* \* \* \* \*